United States Patent
Hoffmann et al.

(10) Patent No.: US 6,398,809 B1
(45) Date of Patent: Jun. 4, 2002

(54) INTRAOCULAR LENS

(75) Inventors: Laurent Hoffmann, Foothill Ranch; Donald C. Stenger, Anaheim Hills; Eric Wilde, Rancho Cucamonga; Charles J. Hagemeier, Laguna Beach, all of CA (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/548,137

(22) Filed: Apr. 12, 2000

(51) Int. Cl.$^7$ .................................................. A61F 2/16
(52) U.S. Cl. ...................................... 623/6.49; 623/6.43
(58) Field of Search ........................... 623/6, 6.49, 6.52, 623/6.53, 6.43

(56) References Cited

U.S. PATENT DOCUMENTS

| | | |
|---|---|---|
| 3,721,657 A | 3/1973 | Seiderman et al. ............. 623/6 |
| 3,792,028 A | 2/1974 | Seiderman ....................... 623/6 |
| 3,961,379 A | 6/1976 | Highgate ......................... 623/6 |
| 4,073,015 A | 2/1978 | Peyman et al. ................. 623/6 |

(List continued on next page.)

FOREIGN PATENT DOCUMENTS

| | | |
|---|---|---|
| AU | B-331730/84 | 8/1983 |
| DE | 2717706 | 4/1977 |
| DE | 3439551 A1 | 10/1984 |
| EP | 0136807 | 8/1984 |
| EP | 391452 B1 | 8/1984 |
| EP | 0118985 | 9/1984 |
| FR | 1103399 | 11/1955 |
| GB | 2114315 A | 8/1983 |
| GB | 2151371 A | 7/1985 |
| WO | WO 87/01931 | 4/1987 |

*Primary Examiner*—David J. Isabella
*Assistant Examiner*—Urmi Chattopadhyay
(74) *Attorney, Agent, or Firm*—Rita D. Vacca (57) ABSTRACT

A refractive anterior chamber intraocular lens including an optic portion having an outer peripheral edge and two or more but preferably three or four haptic elements. Each haptic element is of like form. Each haptic element is also manufactured to have an inner portion and an outer portion for supporting the optic portion in a patient's eye. The inner portion of each haptic element is preferably permanently connected to the outer peripheral edge of the optic portion. Each haptic element also includes a contact button and a central portion located between the contact button and the inner portion. Each haptic is formed to have greater resistance to bending in a plane generally parallel to an eye's optical axis than in a plane generally perpendicular to the eye's optical axis. The intraocular lens is so designed to exhibit less than approximately 1.0 mm axial displacement of the optic portion along the eye's optical axis under a compression force suitable to effect a 1.0 mm in diameter compression of the intraocular lens.

20 Claims, 4 Drawing Sheets

U.S. PATENT DOCUMENTS

| | | | |
|---|---|---|---|
| 4,242,762 A | 1/1981 | Tennant | 623/6 |
| 4,249,272 A | 2/1981 | Poler | 623/6 |
| 4,254,509 A | 3/1981 | Tennant | 623/6 |
| 4,254,510 A | 3/1981 | Tennant | 623/6 |
| 4,261,065 A | 4/1981 | Tennant | 623/6 |
| 4,277,852 A | 7/1981 | Poler | 623/6 |
| 4,315,336 A | 2/1982 | Poler | 623/6 |
| 4,316,293 A | 2/1982 | Bayers | 623/6 |
| 4,377,873 A | 3/1983 | Reichert, Jr. | 623/6 |
| 4,403,353 A | 9/1983 | Tennant | 623/6 |
| 4,424,597 A | 1/1984 | Schlegel | 623/6 |
| 4,446,581 A | 5/1984 | Blake | 623/6 |
| RE31,640 E | 8/1984 | Freeman | 623/6 |
| 4,556,998 A | 12/1985 | Siepser | 623/6 |
| 4,573,998 A | 3/1986 | Mazzocco | 623/6 |
| 4,575,374 A | 3/1986 | Anis | 623/6 |
| 4,575,878 A | 3/1986 | Dubroff | 623/6 |
| 4,585,456 A | 4/1986 | Blackmore | 623/6 |
| 4,605,409 A | 8/1986 | Kelman | 623/6 |
| 4,605,411 A | 8/1986 | Fedorov et al. | 623/6 |
| 4,615,702 A | 10/1986 | Koziol et al. | 623/6 |
| 4,629,460 A | 12/1986 | Dyer | 623/6 |
| 4,629,462 A | 12/1986 | Feaster | 623/6 |
| 4,634,441 A | 1/1987 | Clayman et al. | 623/6 |
| 4,642,113 A | 2/1987 | Dubroff | 623/6 |
| 4,642,116 A | 2/1987 | Clayman et al. | 623/6 |
| 4,664,666 A | 5/1987 | Barrett | 623/6 |
| 4,673,406 A | 6/1987 | Schlegel | 623/6 |
| 4,676,791 A | 6/1987 | LeMaster et al. | 623/6 |
| 4,676,792 A | 6/1987 | Praeger | 623/6 |
| 4,687,485 A | 8/1987 | Lim et al. | 623/6 |
| RE32,525 E | 10/1987 | Pannu | 623/6 |
| 4,718,904 A | 1/1988 | Thornton | 623/6 |
| 4,718,906 A | 1/1988 | Mackool | 623/6 |
| 4,725,277 A | 2/1988 | Bissonette | 623/6 |
| 4,734,095 A | 3/1988 | Siepser | 623/6 |
| 4,769,035 A | 9/1988 | Kelman | 623/6 |
| 4,781,717 A | 11/1988 | Grendahl | 623/6 |
| 4,787,904 A | 11/1988 | Severin et al. | 623/6 |
| RE33,039 E | 8/1989 | Arnott | 623/6 |
| 4,863,466 A | 9/1989 | Schlegel | 623/6 |
| 4,932,970 A | 6/1990 | Portney | 623/6 |
| 4,936,850 A | 6/1990 | Barrett | 623/6 |
| 4,997,442 A | 3/1991 | Barret | 623/6 |
| 5,002,568 A | 3/1991 | Katzen | 623/6 |
| 5,047,052 A | 9/1991 | Dubroff | 623/6 |
| 5,066,301 A | 11/1991 | Wiley | 623/6 |
| 5,071,432 A | 12/1991 | Baikoff | 623/6 |
| 5,078,742 A | 1/1992 | Dahan | 623/6 |
| 5,092,880 A | 3/1992 | Ohmi | 623/6 |
| 5,100,226 A | 3/1992 | Freeman | 623/6 |
| 5,108,429 A | 4/1992 | Wiley | 623/6 |
| 5,133,749 A | 7/1992 | Nordan | 623/6 |
| 5,147,395 A | 9/1992 | Willis | 623/6 |
| 5,171,266 A | 12/1992 | Wiley et al. | 623/6 |
| 5,196,026 A | 3/1993 | Barrett, et al. | 623/6 |
| 5,197,981 A | 3/1993 | Southard | 623/6 |
| 5,203,788 A | 4/1993 | Wiley | 623/6 |
| 5,203,790 A | 4/1993 | McDonald | 623/6 |
| 5,211,662 A | 5/1993 | Barrett et al. | 623/6 |
| 5,217,491 A | 6/1993 | Vanderbilt | 623/6 |
| 5,222,981 A | 6/1993 | Werblin | 623/6 |
| 5,258,025 A | 11/1993 | Fedorov et al. | 623/6 |
| 5,336,261 A | 8/1994 | Barrett et al. | 623/6 |
| 5,476,514 A | 12/1995 | Cumming | 623/6 |
| 5,716,403 A | 2/1998 | Tran et al. | 623/6 |
| 6,228,115 B1 * | 5/2001 | Hoffmann et al. | 623/6.49 |

\* cited by examiner

INTRAOCULAR LENS

FIELD OF THE INVENTION

The present invention relates to intraocular lenses (IOLs) and a method for making and using the same. More particularly, the present invention relates to IOLs designed primarily for refractive correction in phakic eyes where the eye's natural lens remains intact.

BACKGROUND OF THE INVENTION

Visual acuity deficiencies such as myopia (nearsightedness), hyperopia (farsightedness), presbyopia (age-related farsightedness), aphakia (absence of the crystalline lens of the eye) and astigmatism (irregular conformation of the cornea of the eye) are typically corrected through the use of refractive lenses such as spectacles or contact lenses. Although these types of lenses are effective in correcting a wearer's eyesight, many wearers consider the lenses inconvenient. The lenses must be located, worn at certain times, removed periodically and may be lost or misplaced. The lenses may also be dangerous or cumbersome if the wearer participates in athletic activities or suffers an impact in an area near the eyes.

The use of surgically implanted anterior chamber IOLs as a permanent form of refractive correction has been gaining in popularity. IOL implants have been used for years in the anterior or posterior chamber of aphakic eyes as replacements for diseased natural crystalline lenses that have been surgically removed from the eyes. Many different IOL designs have been developed over past years and proven successful for use in aphakic eyes. The successful IOL designs to date primarily include an optic portion with supports therefor, called haptics, connected to and surrounding at least part of the optic portion. The haptic portions of an IOL are designed to support the optic portion of the IOL in the lens capsule, anterior chamber or posterior chamber of an eye once implanted.

Commercially successful IOLs have been made from a variety of biocompatible materials, ranging from more rigid materials such as polymethylmethacrylate (PMMA) to softer, more flexible materials capable of being folded or compressed such as silicones, certain acrylics, and hydrogels. Haptic portions of the IOLs have been formed separately from the optic portion and later connected thereto through processes such as heat, physical staking and/or chemical bonding. Haptics have also been formed as an integral part of the optic portion in what is commonly referred to as "single-piece" IOLs.

Softer, more flexible IOLs have gained in popularity in recent years due to their ability to be compressed, folded, rolled or otherwise deformed. Such softer IOLs may be deformed prior to insertion thereof through an incision in the cornea of an eye. Following insertion of the IOL in an eye, the IOL returns to its original pre-deformed shape due to the memory characteristics of the soft material. Softer, more flexible IOLs as just described may be implanted into an eye through an incision that is much smaller, i.e., 2.8 to 3.2 mm, than that necessary for more rigid IOLs, i.e., 4.8 to 6.0 mm. A larger incision is necessary for more rigid IOLs because the lens must be inserted through an incision in the cornea slightly larger than that of the diameter of the inflexible IOL optic portion. Accordingly, more rigid IOLs have become less popular in the market since larger incisions have been found to be associated with an increased incidence of postoperative complications, such as induced astigmatism.

After IOL implantation, both softer and more rigid IOLs are subject to compressive forces exerted on the outer edges thereof, which typically occur when an individual squints or rubs the eye. This is particularly true of IOLs implanted in the anterior chamber of an eye. Such compressive forces on an IOL may result in tissue damage, decentration of the IOL and/or distortion of the visual image. Compressive forces exerted on an IOL also tend to cause movement of the IOL haptics and axial displacement of the IOL along the optical axis of an eye. Haptic movement and broad haptic contact in the angle of the anterior chamber of an eye has the potential to cause damage to delicate structures within the eye such as the peripheral corneal endothelium, the trabecular meshwork and/or the iris. Movement of an IOL along the optical axis of an eye has the potential to cause the IOL to contact and damage the delicate corneal endothelial cell layer of the eye. Also, IOLs of current designs, whether formed of either softer or more rigid materials, tend to deflect along the optical axis of an eye when the haptics are compressed. IOL manufacturers provide a wide range of IOL sizes to more precisely fit IOLs to each particular patient's eye size. Providing a wide range of IOL sizes is an attempt to minimize the potential for haptic compression and the associated axial displacement of the IOL optic along the optical axis of an eye.

Because of the noted shortcomings of current IOL designs, there is a need for IOLs designed to minimize haptic contact and movement in the angle of the anterior chamber and to minimized axial displacement of the IOL optic portion along the optical axis of the eye when compressive forces are exerted against the outer edges thereof. By lessening an IOL's optic and haptic movement, more certain refractive correction may be achieved and the risk of delicate tissue damage may be reduced.

SUMMARY OF THE INVENTION

An anterior chamber intraocular lens (IOL) made in accordance with the present invention has an optic portion with an outer peripheral edge and two or more but preferably three or four haptic elements for supporting the optic portion in a patient's eye. Three or four haptic elements are preferred in the present invention to provide a balance between IOL stability and minimized haptic contact in the angle of the anterior chamber. A lens having three haptic elements is balanced or stabilized by having two spaced haptic elements formed on one edge of the optic and the third haptic element formed on an opposite edge of the optic or alternatively stabilized by having each of the three haptic elements spaced on the edge of the optic with an equal distance therebetween. A lens having four haptic elements is balanced or stabilized by having two spaced haptic elements formed on one edge of the optic and two spaced haptic elements formed on an opposite edge of the optic or alternatively stabilized by having each of the four haptic elements spaced on the edge of the optic with an equal distance therebetween. Each of the haptic elements is of like form to achieve a rotational effect for ease of implantation, turning and centering of the IOL and to achieve the desired rotation and flexure functions described in greater detail below. Each of the haptic elements also has an inner portion and an outer portion with the inner portion being connected to the outer peripheral edge of the optic portion. Each haptic element includes a contact button or small knob on the outer portion thereof. The contact buttons are designed to minimally engage inner surfaces of a patient's eye.

Each haptic element also has a central portion that extends between the contact button and the inner portion. Within this central portion, each haptic element is designed to have greater resistance to bending in a plane generally parallel to the optical axis of an eye than in a plane generally perpendicular to the optical axis of an eye. By providing haptic elements with this type of flexibility characteristic, the present IOL fits eyes of varying sizes. The flexibility characteristic of the subject haptic elements relative to the optic portion eliminates unacceptable axial displacement of the optic portion along the optical axis of an eye when compressive forces are exerted against the haptic elements of the IOL. In the present IOL, compressive forces are not dispersed through axial displacement of the optic portion, but rather through planar, rotational movement of the optic portion.

Accordingly, it is an object of the present invention to provide intraocular lenses for use in phakic eyes.

Another object of the present invention is to provide intraocular lenses for use in phakic eyes, which fit a variety of eye sizes.

Another object of the present invention is to provide intraocular lenses for use in phakic eyes, which minimize axial displacement of the optic portions of the lenses along the optical axis of the eyes.

Another object of the present invention is to provide intraocular lenses that allow for increased ease of implantation, turning and centering of the same.

Another object of the present invention is to provide intraocular lenses for use in phakic eyes, which minimize damage to tissues in the interior of the eyes.

Still another object of the present invention is to provide intraocular lenses, which are resistant to decentration within the eyes.

These and other objectives and advantages of the present invention, some of which are specifically described and others that are not, will become apparent from the detailed description, drawings and claims that follow, wherein like features are designated by like numerals.

DETAILED DESCRIPTION OF THE INVENTION

Figure 1:
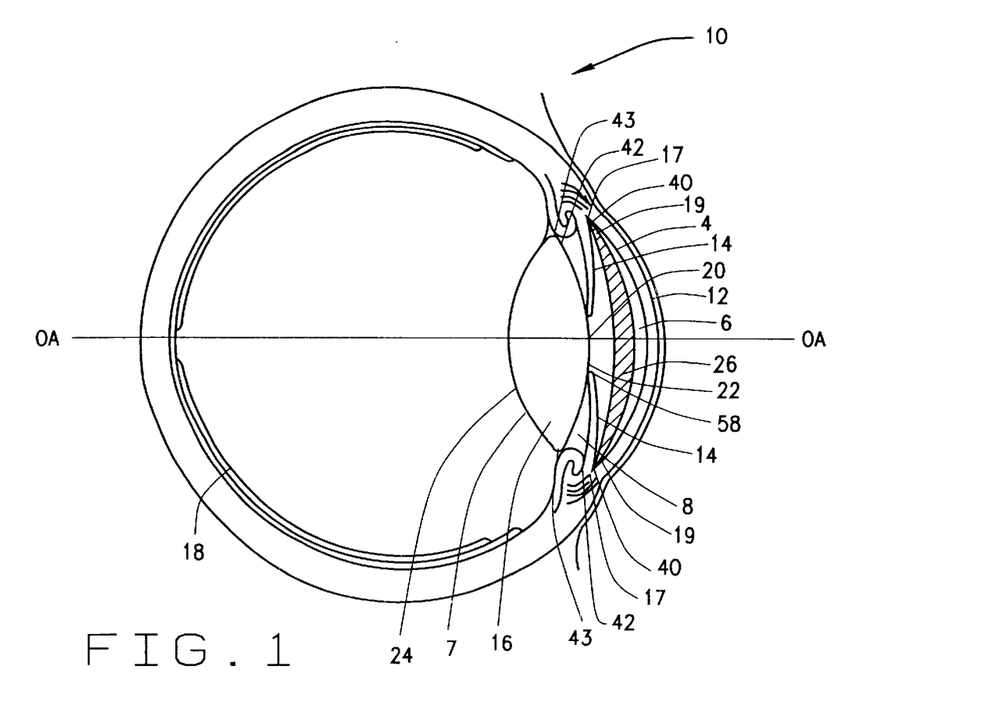
FIG. 1 is a schematic representation of the interior of a human eye including a natural lens and a refractive IOL implanted in the anterior chamber of the eye.

FIG. 1 illustrates a simplified diagram of an eye 10 showing landmark structures relevant to the implantation of an intraocular lens of the present invention. Eye 10 includes an optically clear cornea 12 and an iris 14. A natural crystalline lens 16 and a retina 18 are located behind the iris 14 of eye 10. Eye 10 also includes anterior chamber 6 located in front of iris 14 and a posterior chamber 8 located between iris 14 and natural lens 16. An IOL 26, such as that of the present invention, is preferably implanted in anterior chamber 6 to correct refractive errors while healthy natural lens 16 remains in place (phakic application). IOLs of the present invention may also be implanted in posterior chamber 8 or lens capsule 7 for use in aphakic eyes. When used in aphakic eyes, IOLs serve as replacements for surgically removed diseased natural lenses 16, such as for example following cataract surgeries. Eye 10 also includes an optical axis OA—OA that is an imaginary line that passes through the optical center 20 of anterior surface 22 and posterior surface 24 of lens 16. Optical axis OA—OA in the human eye 10 is generally perpendicular to a portion of cornea 12, natural lens 16 and retina 18.

Figure 2:
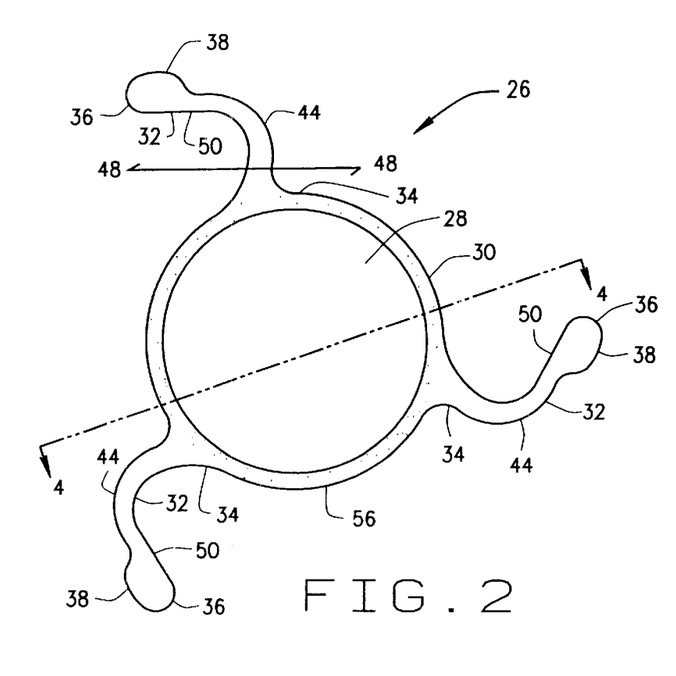
FIG. 2 is a plan view of an IOL with three haptics made in accordance with the present invention.
Figure 3:
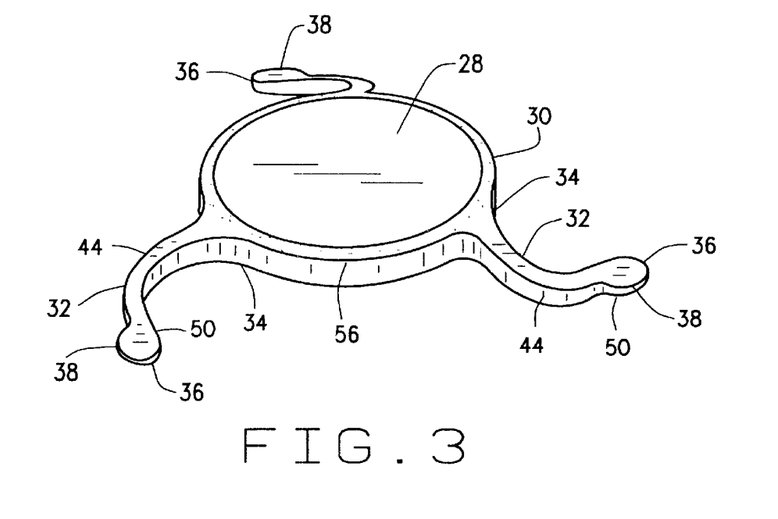
FIG. 3 is a perspective view of the IOL of FIG. 2.
Figure 9:
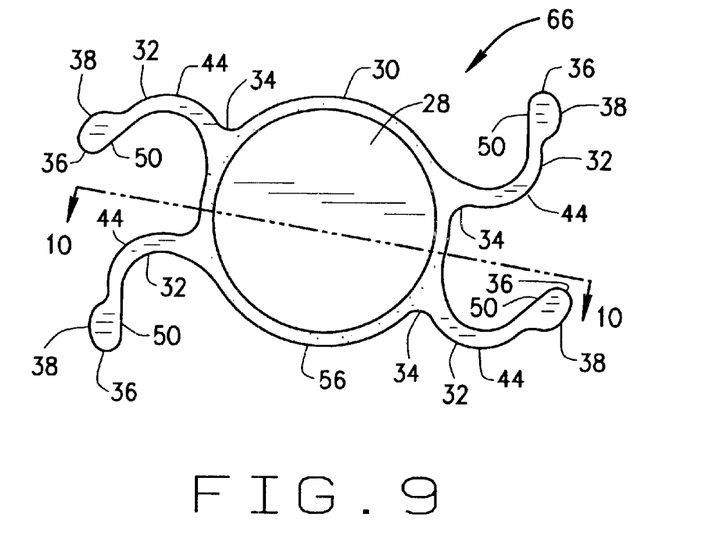
FIG. 9 is a plan view of an IOL with four haptics made in accordance with the present invention.

The IOL of the present invention, as best illustrated in FIGS. 2, 3 and 9 identified by reference numeral 26, is designed for implantation preferably in anterior chamber 6 of a patient's eye 10. However as mentioned above, IOL 26 may likewise be implanted in posterior chamber 8 or in the case of an aphakic eye, in lens capsule 7. IOL 26 has an optic portion 28 with an outer peripheral edge 30. Preferably integrally formed on peripheral edge 30 of optic portion 28 are two or more but preferably three or four separate haptic elements 32, each of like form to achieve a rotational design for ease in turning and centering IOL 26 upon implantation thereof within an eye and to achieve the desired rotation and flexure functions as described further herein. Each haptic element 32 is manufactured to have an inner portion 34 and an outer portion 36. Inner portions 34 of haptic elements 32 are preferably integrally formed with and permanently connected to outer peripheral edge 30 of optic portion 28. Alternatively however, inner portions 34 of haptic elements 32 may be attached to optic portion 28 by staking, chemical polymerization or other methods known to those skilled in the art. Each haptic element 32 also includes at outer portion 36, a radially protruding contact button 38 designed to preferably engage inner surfaces 40 in anterior chamber 6. However, contact buttons 38 are also suitable to engage inner surfaces 42 in posterior chamber 8 or inner surfaces 43 in lens capsule 7 of an aphakic eye 10. In accordance with the present invention, haptic elements 32 are designed so that when IOL 26 is implanted in a patient's phakic or aphakic eye 10 and held in place through compressive forces exerted by inner surfaces 40, 42 or 43 on contact buttons 38 of haptic elements 32, haptic elements 32 flex so that contact buttons 38 do not slide or move along surfaces 40, 42 or 43 in the eye 10. Sliding and movement of contact buttons 38 is avoided in the subject IOL 26 to minimize tissue damage. Accordingly, haptic elements 32 are designed to flex in a plane generally parallel to that of optic portion 28 of IOL 26 and generally perpendicular to that of optical axis OA—OA of eye 10. By designing this type of flexibility characteristic into haptic elements 32 all of the same form, compression forces on haptic elements 32 are dispersed through planar rotational movement of optic portion 28. Such rotation and flexure characteristics of the subject IOL 26 allows the same to be manufactured in one or a few standard sizes and be a suitable fit for most sizes of patients' eyes 10. The flexure and rotation characteristics of IOL 26 also minimize axial displacement of optic portion 28 in a direction along optical axis OA—OA of eye 10. Compressive forces on haptic elements 32 are dispersed through rotational movement of optic portion 28 in a plane perpendicular to the optical axis OA—OA of the eye rather than through axial displacement of the optic portion. Compressive forces of differing magnitudes within the range of approximately 0.2 to 1.0 mN exerted against contact buttons 38 of haptic elements 32 to effect approximately an overall 1.0 mm in diameter compression of IOL 26, such as that caused by differing eye sizes, sleep pressure, eye rubbing and/or other externally applied post implantation forces, results in less than approximately 1.0 mm, but more preferably less than approximately 0.5 mm and most preferably less than approximately 0.3 mm axial displacement of optic portion 28 along optical axis OA—OA in an eye 10. Under like compressive forces, IOLs known in the art result in approximately 2.0 mm axial displacement of the optic portion along the optical axis in the eye, which may damage delicate tissues therein. The unique design of IOL 26 achieves significantly minimized axial displacement of optic portion 28 to protect the corneal endothelium 4 of eye 10 from damage when compressive forces are applied to eye 10. By minimizing axial displacement of IOL 26, harmful contact with corneal endothelium 4 is also minimized.

Figure 4:
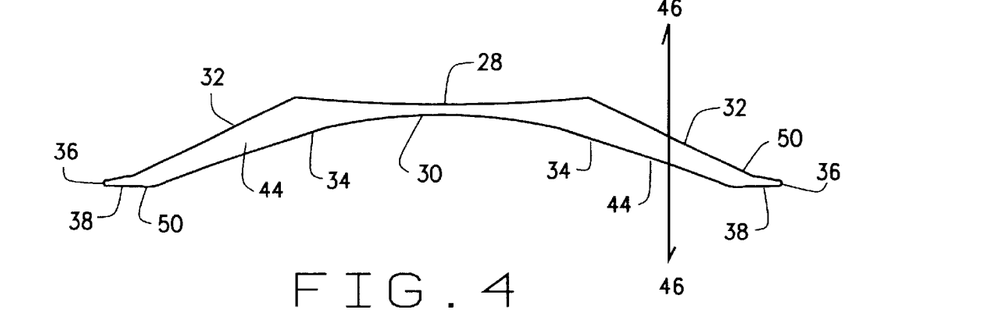
FIG. 4 is a side cross sectional view of the IOL of FIG. 2 taken along line 4—4.
Figure 5:
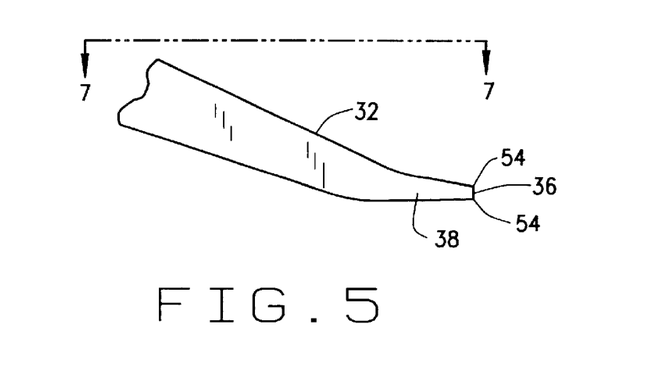
FIG. 5 is a side view of a haptic element of FIG. 2 with sharper edges.
Figure 6:
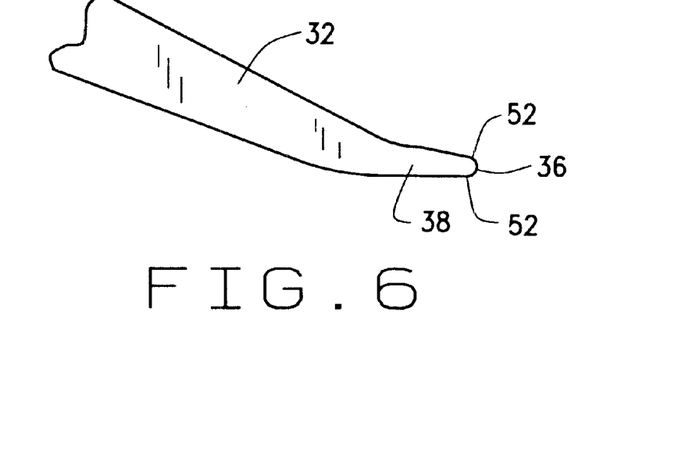
FIG. 6 is a side view of a haptic element of FIG. 2 with rounder edges.
Figure 8:
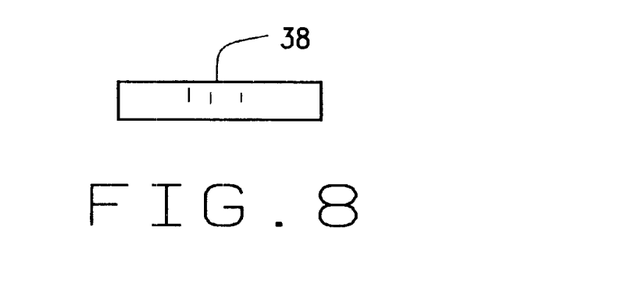
FIG. 8 is a side view of the contact button on the haptic of the IOL of FIG. 2.
Figure 10:
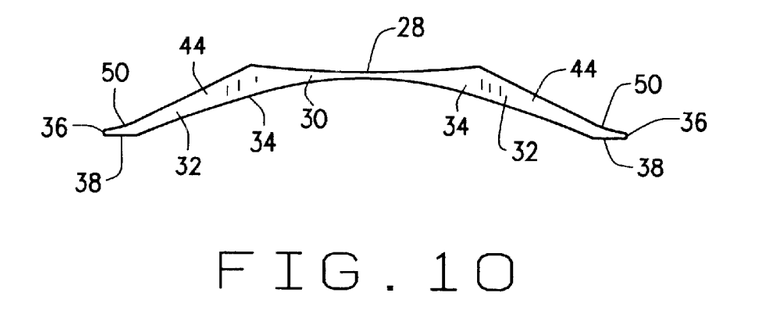
FIG. 10 is a side cross sectional view of the IOL of FIG. 9 taken along line 10—10.
Figure 11:
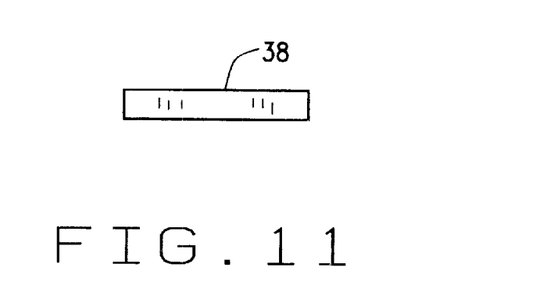
FIG. 11 is a side view of the contact button on the haptic of the IOL of FIG. 9.

The flexibility characteristic of haptic elements 32 of IOL 26 as described above is achieved through the unique design thereof. IOL 26 has haptic elements 32 formed with a central portion 44 adjacent to inner portion 34 permanently connected to outer peripheral edge 30 of optic portion 28. As best illustrated in FIGS. 4 and 10, central portion 44 has a dimension in plane 46—46, generally parallel to optical axis OA—OA, equal to or greater than the same in plane 48—48 generally perpendicular to optical axis OA—OA best depicted in FIGS. 2 and 9. A transition portion 50, of significantly decreasing size in dimension in plane 46—46 extends from central portion 44 to contact button 38. Contact buttons 38 are relatively small radially protruding knobs as best illustrated in FIGS. 8 and 11. The outer portions 36 which support contact buttons 38 may be formed with either rounded edges 52 depicted in FIG. 6 for a smoother more contoured appearance or formed with more defined, sharper edges 54 as depicted in FIG. 5.

The subject IOL 26 is preferably produced having an optic portion 28 approximately 4.5 to 9.0 mm, but preferably approximately 5.0 to 6.0 mm and most preferably 5.5 mm in diameter and approximately 0.5 mm to 1.0 mm, but preferably approximately 0.6 to 0.8 mm and most preferably 0.7 mm in thickness at peripheral edge 30. Haptic elements 32 extend in a curved configuration and will increase or decrease in length depending upon the diameter of optic portion 28. As the diameter of optic portion 28 increases, the length of haptic elements 32 decrease. Likewise, as the diameter of optic portion 28 decreases, the length of haptic elements 32 increase. In general, haptic elements 32 are formed to be approximately 2.6 to 6.0 mm, but preferably approximately 3.4 to 5.0 mm and most preferably approximately 4.2 mm in length measuring from the center of inner portion 34 to the center of outer portion 36. Haptic elements 32 are preferred to have curved configurations of like form as illustrated in FIGS. 2 and 9 to rotationally disperse compressive forces while outer portions 36 and contact buttons 38 remain stationary. For purposes of the present invention, the curved shape of haptic element 32, i.e., the beam curve shape, relative to the width to thickness ratio, i.e., the aspect ratio, of haptic element 32 as described herein is critical to achieve suitable rotation and flexure functions. Central portion 44 of haptic element 32 is approximately 0.5 to 2.5 mm, but preferably approximately 1.0 to 2.0 mm and most preferably 1.6 mm in length; approximately 0.2 to 1.0 mm, but preferably approximately 0.3 to 0.7 mm and most preferably approximately 0.46 mm in thickness in plane 46—46 and approximately 0.2 to 0.7 mm, but preferably approximately 0.3 to 0.6 and most preferably approximately 0.43 mm in width in plane 48—48. Transition portion 50 is approximately 0.4 to 1.1 mm, but preferably approximately 0.5 to 1.0 mm and most preferably approximately 0.8 mm in length. Contact buttons 38 are approximately 0.2 to 1.0 mm, but preferably approximately 0.4 to 0.6 mm and most preferably approximately 0.5 mm in diameter and approximately 0.05 to 0.5 mm, but preferably approximately 0.1 to 0.4 mm and most preferably approximately 0.3 mm in thickness. Contact buttons 38 illustrated in FIGS. 2, 3, 8, 9 and 11 are relatively small, thin radially protruding knobs to minimize the area of contact and movement in the angle 19 of the anterior chamber 6.

As provided through the dimensions of IOL 26 above, haptic elements 32 gradually change from being relatively thin in plane 46—46 at outer portion 36 to being relatively thick at inner portion 34 and optic portion 28, with central portion 44 exhibiting a thicker dimension in plane 46—46 than that of the width in plane 48—48. Haptic elements 32 of the subject design tend to flex with rotational movement of optic portion 28 when a compression force is exerted against contact buttons 38. With the conversion of energy from compression forces on haptic elements 32 into rotational energy of optic portion 28, axial displacement along optical axis OA—OA is minimized and movement of haptic elements 32 is minimized. When IOL 26 is used as a refractive lens, a stable, reliable refractive correction is provided with minimal damage to delicate tissues within the eye.

Figure 7:
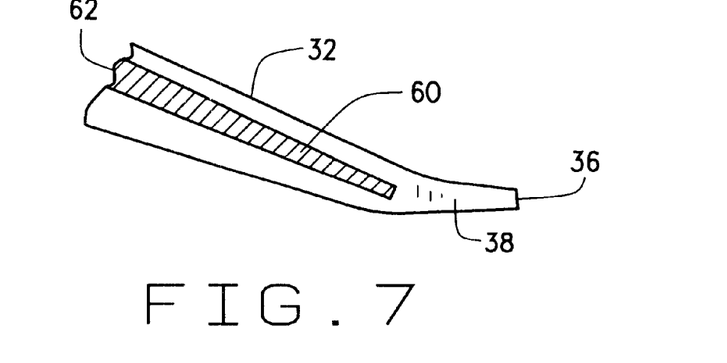
FIG. 7 is a side cross sectional view of a haptic element of FIG. 5 taken along line 7—7 with a stiffening element.

The desired rotation and flexure characteristics of IOL 26 may likewise be achieved or enhanced by incorporating a stiffening element 60, in the shape of a ribbon, in one or more haptic elements 32, as illustrated in FIG. 7. Stiffening element 60 may be positioned in haptic element 32 so that flat face 62 is oriented parallel to the dimension 46—46. Stiffening element 60 functions in a manner similar to that of an I-beam in construction to prevent axial displacement along optical axis OA—OA when compressive force is applied to contact buttons 38.

Stiffening element 60 is formed of a less flexible material than that of IOL 26. Suitable materials for stiffening element 60 include but are not limited to polyimides, polyolefins, high-density polyethylenes, polyesters, nylons, metals or any biocompatible material with suitable stiffening characteristics. Stiffening element 60 may be used in conjunction with haptic elements 32 described above or in cases where a thinner haptic design is desired while still achieving the desired rotation and flexure characteristics.

Suitable materials for the production of the subject IOL 26 include but are not limited to foldable or compressible materials, such as silicone polymers, hydrocarbon and fluorocarbon polymers, hydrogels, soft acrylic polymers, polyesters, polyamides, polyurethane, silicone polymers with hydrophilic monomer units, fluorine-containing polysiloxane elastomers and combinations thereof. The preferred material for the production of IOL 26 of the present invention is a hydrogel made from 2-hydroxyethyl methacrylate (HEMA) and 6-hydroxyhexyl methacrylate (HOHEXMA), i.e., poly(HEMA-co-HOHEXMA). Poly(HEMA-co-HOHEXMA) is the preferred material for the manufacture of IOL 26 due to its equilibrium water content of approximately 18 percent by weight, and high refractive index of approximately 1.474, which is greater than that of the aqueous humor of the eye, i.e., 1.33. A high refractive index is a desirable feature in the production of IOLs to impart high optical power with a minimum of optic thickness. By using a material with a high refractive index, visual acuity deficiencies may be corrected using a thinner IOL. A thin IOL, such as that of IOL 26, is particularly desirable in phakic applications to minimize potentially harmful contact between the IOL and the iris 14 and the corneal endothelium 4. Poly(HEMA-co-HOHEXMA) is also a desirable material in the production of IOLs 26 due to its mechanical strength, which is suitable to withstand considerable physical manipulation. Poly(HEMA-co-HOHEXMA) also has desirable memory properties suitable for IOL use. IOLs manufactured from a material possessing good memory properties such as those of poly(HEMA-co-HOHEXMA) unfold in a controlled manner in an eye, rather than explosively, to its predetermined shape. Explosive unfolding of IOLs is undesirable due to potential damage to delicate tissues within the eye. Poly(HEMA-co-HOHEXMA) also has dimensional stability in the eye.

Although the teachings of the present invention are preferably applied to soft or foldable IOLs formed of a foldable or compressible material, the same may also be applied to harder, less flexible lenses formed of a relatively rigid material such as polymethylmethacrylate (PMMA) having flexible haptics formed either of the same or a different material.

Optic portion 28 of IOL 26 can be a positive powered lens from 0 to approximately +40 diopters or a negative powered lens from 0 to approximately −30 diopters. Optic portion 28 may be biconvex, plano-convex, plano-concave, biconcave or concave-convex (meniscus), depending upon the power required to achieve the appropriate central and peripheral thickness for efficient handling.

Optic portion 28 of the subject IOL 26 may optionally be formed with a glare reduction zone 56 of approximately 0.25 to 0.75 mm but more preferably approximately 0.3 to 0.6 mm and most preferably 0.5 mm in width adjacent to the outer peripheral edge 30 for reducing glare when outer peripheral edge 30 of IOL 26 is struck by light entering eye 10 during high light or at other times when pupil 58 is dilated. Glare reduction zone 56 is typically fabricated of the same material as optic portion 28, but may be opaque, colored or patterned in a conventional manner to block or diffuse light in plane with optical axis OA—OA.

Subject IOL 26 may be molded using a removable mold as known to those skilled in the art or may be manufactured by first producing discs from a material of choice as described in U.S. Pat. Nos. 5,217,491 and 5,326,506 each incorporated herein in its entirety by reference. IOL 26 may then be machined from the material discs in a conventional manner. Once machined, IOL 26 may be polished, cleaned, sterilized and packaged by a conventional method known to those skilled in the art.

Subject IOL 26 is used in eye 10 by creating an incision in cornea 12, inserting IOL 26 in either anterior chamber 6 or posterior chamber 8 and closing the incision in accordance with methods known to those skilled in the art. Alternatively, IOL 26 may be used in eye 10 by creating an incision in cornea 12 and capsule 7, removing natural lens 16, inserting IOL 26 in capsule 7 and closing the incision in accordance with methods known to those skilled in the art.

IOL 26 of the present invention provides for a refractive lens suitable for use in lens capsule 7 or posterior chamber 8, but most preferably for use in anterior chamber 6 of eye 10. IOL 26 has haptic elements 32 of like form with rotation and flexure characteristics that minimize axial displacement along optical axis OA—OA of eye 10 thereby preventing decentration of IOL 26, distortion of vision and damage to delicate eye tissues such as the natural lens 16, trabecular meshwork 17, the corneal endothelium 4 and the iris 14. IOL 26, having the rotation and flexure characteristics described herein is also advantageous because one or a few lens sizes suitably fit eyes 10 of most sizes. By providing a "universal" lens such as that of the present invention, clinical risks to patients due to improperly sized lenses are minimized. Such clinical risks minimized include pupil ovalization, corneal endothelium damage and poor fixation. Likewise, manufacturers' need to produce IOLs of many sizes to fit eyes of many sizes is eliminated, thus reducing production and inventory costs associated therewith. Ophthalmologists also benefit from subject IOL 26 in that time is saved by eliminating the need to determine each patient's eye size and costs associated with maintaining large inventories of varying sized lenses.

While there is shown and described herein certain specific embodiments of the present invention, it will be manifest to those skilled in the art that various modifications may be made without departing from the spirit and scope of the underlying inventive concept and that the same is not limited to the particular forms herein shown and described except insofar as indicated by the scope of the appended claims.

We claim:

1. An intraocular lens to be implanted within an eye generally perpendicular to the eye's optical axis comprising:
   an outer peripheral edge defining an optic portion;
   two or more haptic elements of like form, like directional inward flexation and non-uniform cross section throughout, permanently connected to the outer peripheral edge;
   central portions formed in each haptic element having a greater resistance to bending in a plane parallel to the eye's optical axis than in a plane perpendicular thereto to cause a compressive force sufficient to effect a 1.0 mm in diameter compression of said lens to result in rotational movement of said optic portion and less than approximately 1.0 mm of axial displacement of said optic portion; and
   a contact button on each haptic element to minimize haptic contact within the eye.

2. An intraocular lens to be implanted within an eye generally perpendicular to the eye's optical axis comprising:
   an outer peripheral edge defining an optic portion;
   two or more haptic elements of like form, like directional inward flexation and non-uniform cross section throughout, permanently connected to the outer peripheral edge;
   central portions formed in each haptic element having a greater resistance to bending in a plane parallel to the eye's optical axis than in a plane perpendicular thereto to cause a compressive force sufficient to effect a 1.0 mm in diameter compression of said lens to result in rotational movement of said optic portion and less than approximately 0.5 mm of axial displacement of said optic portion; and
   a contact button on each haptic element to minimize haptic contact within the eye.

3. An intraocular lens to be implanted within an eye generally perpendicular to the eye's optical axis comprising:
   an outer peripheral edge defining an optic portion;
   two or more haptic elements of like form, like directional inward flexation and non-uniform cross section throughout, permanently connected to the outer peripheral edge;

central portions formed in each haptic element having a greater resistance to bending in a plane parallel to the eye's optical axis than in a plane perpendicular thereto to cause a compressive force sufficient to effect a 1.0 mm in diameter compression of said lens to result in rotational movement of said optic portion and less than approximately 0.3 mm of axial displacement of said optic portion; and a contact button on each haptic element to minimize haptic contact within the eye.

4. The intraocular lens of claim 1, 2 or 3 wherein the haptic elements and the optic portion are both formed of a foldable or compressible material.

5. The intraocular lens of claim 1, 2 or 3 wherein said lens is formed from a material selected from the group consisting of silicone polymers, hydrocarbon and fluorocarbon polymers, hydrogels, soft acrylic polymers, polyester, polyamides, polyurethane, silicone polymers with hydrophilic monomer units, fluorine-containing polysiloxane elastomers and combinations thereof.

6. The intraocular lens of claim 1, 2 or 3 wherein said lens is formed from a hydrogel material.

7. The intraocular lens of claim 1, 2 or 3 wherein said lens is formed from a hydrogel material which is 18 percent by weight water.

8. The intraocular lens of claim 1, 2 or 3 wherein said lens is formed from poly(HEMA-co-HOHEXMA).

9. The intraocular lens of claim 1, 2 or 3 wherein said lens is formed from a material having a refractive index above 1.33.

10. The intraocular lens of claim 1, 2 or 3 wherein said lens is formed from an acrylic material.

11. The intraocular lens of claim 1, 2 or 3 wherein said lens is formed from a silicone material.

12. The intraocular lens of claim 1, 2 or 3 wherein said haptic elements are dimensioned to be equal to or less in a plane generally perpendicular to the eye's optical axis than in a plane generally parallel to the eye's optical axis.

13. The intraocular lens of claim 1, 2 or 3 wherein a glare reduction zone is formed adjacent to the outer peripheral edge of the optic portion.

14. The intraocular lens of claim 1, 2 or 3 wherein one or more of said haptic elements includes a stiffening element having a greater resistance to bending in a plane generally parallel to an eye's optical axis than in a plane generally perpendicular to the eye's optical axis.

15. The intraocular lens of claim 1, 2 or 3 wherein the haptic element includes a stiffening element formed from a material selected from the group consisting of polyimide, polyolefin, high-density polyester, nylon and metal.

16. A method of manufacturing the intraocular lens of claim 1, 2 or 3 comprising:

forming a disk of a suitable material, and machining said lens from said disk.

17. A method of manufacturing the intraocular lens of claim 1, 2 or 3 comprising:

molding said lens of a suitable material in a mold, and removing said lens from said mold.

18. A method of using the intraocular lens of claim 1, 2 or 3 comprising:

creating an incision in a cornea of an eye, and inserting said intraocular lens in an anterior chamber of said eye.

19. A method of using the intraocular lens of claim 1, 2 or 3 comprising:

creating an incision in a cornea of an eye, and inserting said intraocular lens in a posterior chamber of said eye.

20. A method of using the intraocular lens of claim 1,2 or 3 comprising:

creating an incision in a cornea and lens capsule of an eye, removing a natural lens of said eye, and inserting said intraocular lens in said lens capsule of said eye.

* * * * *